(12) United States Patent
Cardon

(10) Patent No.: US 6,668,825 B2
(45) Date of Patent: Dec. 30, 2003

(54) VENTILATION TUBE CONNECTION SYSTEM

(76) Inventor: Kerrie Cardon, 6716 46th Ave. SW., Seattle, WA (US) 98136

( * ) Notice: Subject to any disclaimer, the term of this patent is extended or adjusted under 35 U.S.C. 154(b) by 141 days.

(21) Appl. No.: 10/017,696

(22) Filed: Dec. 11, 2001

(65) Prior Publication Data

US 2003/0106558 A1 Jun. 12, 2003

(51) Int. Cl.$^7$ ................................................. A62B 9/04
(52) U.S. Cl. .............................. 128/202.27; 128/207.14
(58) Field of Search ...................... 128/200.14, 200.24, 128/203.12, 202.27, 203.23, 204.18, 207.14–207.18, 911; 285/1, 10, 33, 144.1, 147.1, 148.21, 179, 223, 272, 384–419, 918, 97 C; 138/155

(56) References Cited

U.S. PATENT DOCUMENTS

| | | | | |
|---|---|---|---|---|
| 4,235,229 A | * | 11/1980 | Ranford et al. | ........ 128/207.17 |
| 5,062,420 A | * | 11/1991 | Levine | ................... 128/204.18 |
| 5,184,611 A | * | 2/1993 | Turnbull | ................ 128/207.14 |
| 5,433,195 A | * | 7/1995 | Kee et al. | .............. 128/207.14 |
| 5,694,922 A | * | 12/1997 | Palmer | .................. 128/202.27 |
| 5,702,374 A | * | 12/1997 | Johnson | ...................... 604/283 |
| 2003/0056787 A1 | * | 3/2003 | Svendsen | ............... 128/202.27 |

* cited by examiner

*Primary Examiner*—Glenn K. Dawson
(74) *Attorney, Agent, or Firm*—Dean A. Craine

(57) ABSTRACT

An improved modified ventilation tube system designed to improve patient comfort and prevent accidental "pop off" incidents that often occur with standard endotracheal and ventilation tubes. The system includes a modified endotracheal tube that includes a cylindrical-shaped end adapter, an L-shaped elbow connector with a rotating leg member and a fixed leg member, and a modified ventilation tube. The rotating leg member is perpendicularly aligned on one end of the fixed leg member and slidingly receives the end adapter on the modified endotracheal tube. Disposed around the rotating leg member is a first rotating collar that securely fixes the end adapter to the rotating leg member. The fixed leg member includes a long leg section that slidingly connects to a rotating coupler attached to the modified ventilation tube. A second rotating collar is disposed around the rotating coupler to selectively attach the fixed leg member to the rotating coupler. When the system is assembled, the rotating leg member and rotating coupler are able to selectively rotate over the ends of the elbow connector and the modified ventilation tube, respectively, thereby reducing forces exerted thereon. Optional O-rings are disposed inside each joint to provide airtight seals.

19 Claims, 3 Drawing Sheets

VENTILATION TUBE CONNECTION SYSTEM

BACKGROUND OF THE INVENTION

1. Field of the Invention

This medical invention relates to endotracheal tubes, and more particularly, to endotracheal tubes with quick-connect and disconnect couplers resistant to accidental pop-offs.

2. Description of Prior Art

Patients who are unable to breathe spontaneously require ventilation assistance. Such patients are typically connected to a ventilator, which provides continuous mechanical ventilation assistance.

Connecting the patient to the ventilator requires the use of ventilation tubing that connects to an endotracheal tube placed through the patient's mouth and into the trachea. The connectors between the ends of the ventilation tube and the endotrachael tube utilize a friction-fit connector which may accidentally disconnect, an event known as "pop-off". Disconnection of the connector precludes mechanical ventilation assistance, thereby creating a hazardous situation for the patient. To eliminate "pop-off" events, medical personnel often "tie" the ends of the adjoining tubing together. For patients in a home setting who are not under continuous supervision by medical personnel, "pop-off" events can be fatal. When an endotracheal tube is used, saliva or other secretions accumulate around the end of the endotrachael tube and require periodic suctioning so that the saliva and secretions are not aspirated. In order to perform suctioning, the endotracheal tube must be quickly disconnected from the ventilation tubing and quickly reconnected to a manual ventilation bag. The proximal end of the endotracheal tube must be securely connected to the manual ventilation bag to prevent a "pop-off" event.

SUMMARY OF THE INVENTION it is an object of the present invention to provide an improved ventilation tube connection system designed to prevent a "pop-off" event where the tubing components inadvertently become disconnected.

It is an object of the present invention to provide such a system that uses manual, quick-connect and disconnect connectors between the components.

It is a further object of the present invention to provide such a system that allows a manual ventilation bag to be connected to the proximal end of the modified endotracheal tube so that manual ventilation assistance may be provided.

It is a still further object of the invention to provide such a system that allows the adjoining tube components to be selectively adjusted over the patient to reduce torque forces on the connectors and to improve patient comfort. These and other objects are met by the ventilation tube connection system disclosed herein that includes a modified endotracheal tube, an intermediate elbow connector, and a modified ventilation tube. The modified endotracheal tube includes a main tube section that extends into the throat of the patient and a cylindrical-shaped end adapter attached or integrally formed on the distal end of the main tube section. The end adapter is slightly conical-shaped and designed to slidingly connect to the rotating leg member on the elbow connector, or to a rotating coupler on the modified ventilation tube. A first rotating coupler is used to hold the end adapter on the rotating leg member. Using this design, the end adapter may also slidingly connect to the ventilation tube on a standard, manual ventilation bag.

The elbow connector is a hollow structure comprising a rotating leg-member rotatably attached to an L-shaped fixed member. The fixed member includes a short leg section and a long leg section perpendicularly aligned and integrally formed therewith. During assembly, the rotating leg member is longitudinally aligned and rotatably attached to the short leg section. The opposite end of the rotating leg member is designed to slidingly receive the end adapter on the modified endotracheal tube. Disposed around the rotating leg member is an adjustable collar that securely holds the end adapter inside the rotating leg member.

The long leg section on the elbow connector is designed to selectively connect to a rotating coupler which is used to selectively connect the elbow connector to a modified ventilation tube. In the preferred embodiment, the modified ventilation tube includes a main stem member designed to slidingly connect to the rotating coupler during use. Disposed around the rotating coupler is an adjustable second collar that selectively locks the fixed leg member inside the rotating coupler.

The diameters of the end adaptor, the rotating leg member, the long leg section, and the rotating coupler are sufficient to create airtight connections when the adjoining components are connected together. Optional O-ring seals are disposed between the rotating leg member and the short leg section, and the joint between the rotating coupler and the modified ventilation tube to provide airtight seals between the endotracheal and ventilation tubes and the elbow connector.

When assembled, the rotating leg member, the rotating coupler and the two adjustable collars enable the medical worker to selectively adjust the relative axial orientation of the end adapter on the rotating leg member and the axial orientation of the rotating coupler on the long leg section. When the components are adjusted for greater comfort, the end adapter and rotating coupler are locked in their respective axial positions on the rotating and fixed leg members, respectively. Since the rotating leg member and the rotating coupler are not axially locked in position on the elbow connector and on the modified ventilation tube, respectively, they may axially rotate when torque forces are applied thereto by the endotracheal and modified ventilation tubes thus preventing accidental "pop-offs".

The conical-shape of the end adaptor is also sufficient in diameter so that the complementary-shaped end of a manual ventilation bag may slidingly connect thereto if desired. In addition, the diameters and shapes of the end adapter and rotating coupler are compatible so that the rotating coupler on the modified ventilation tube may directly connect to the end adapter if desired.

DESCRIPTION OF THE PREFERRED EMBODIMENT(S)

Figure 1:
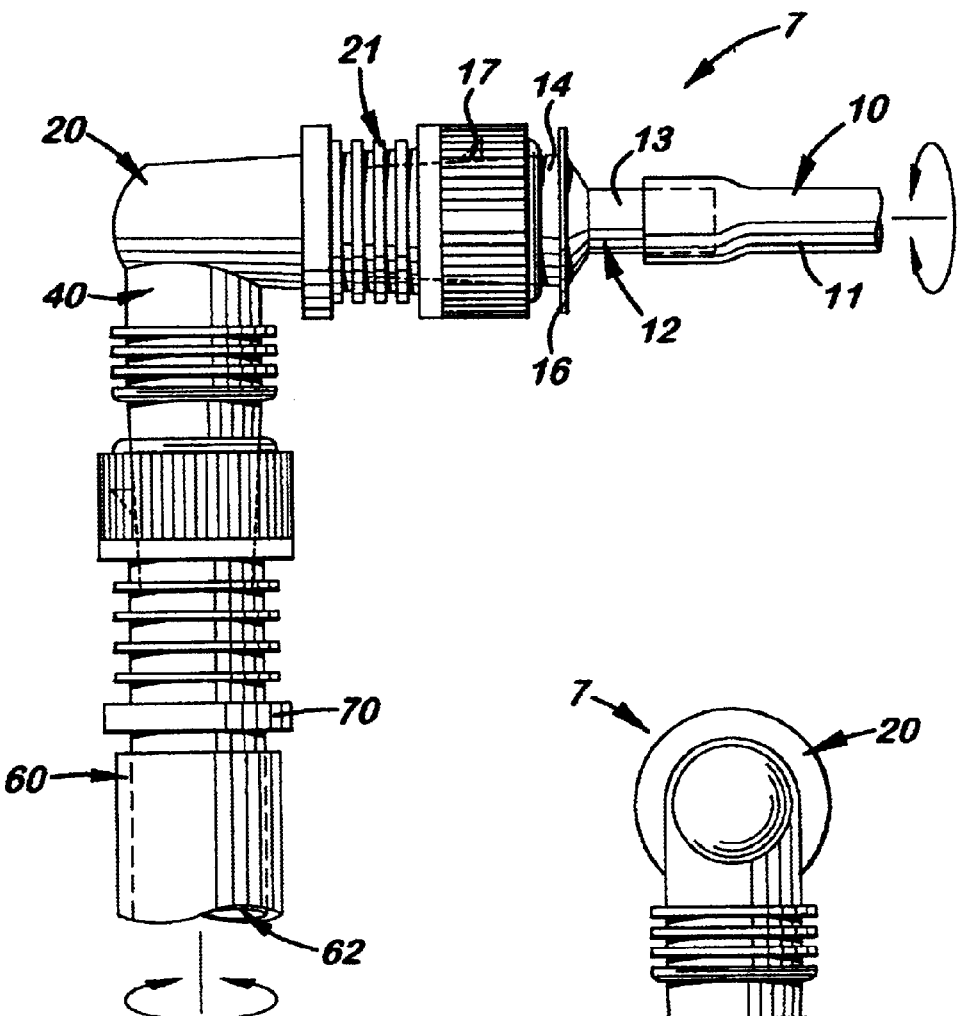
FIG. 1 is a side elevational view of the assembled ventilation tube connection system disclosed herein.
Figure 2:
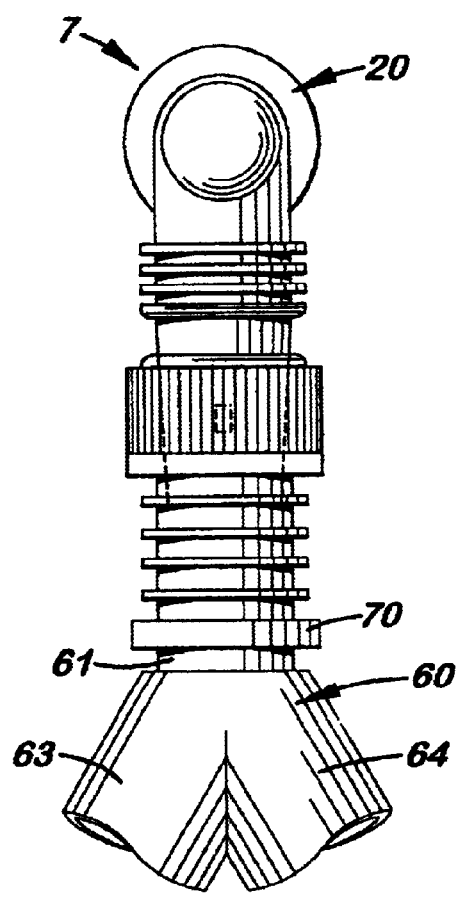
FIG. 2 is a front elevational view of the assembled ventilation tube connection system shown in FIG. 1.
Figure 3:
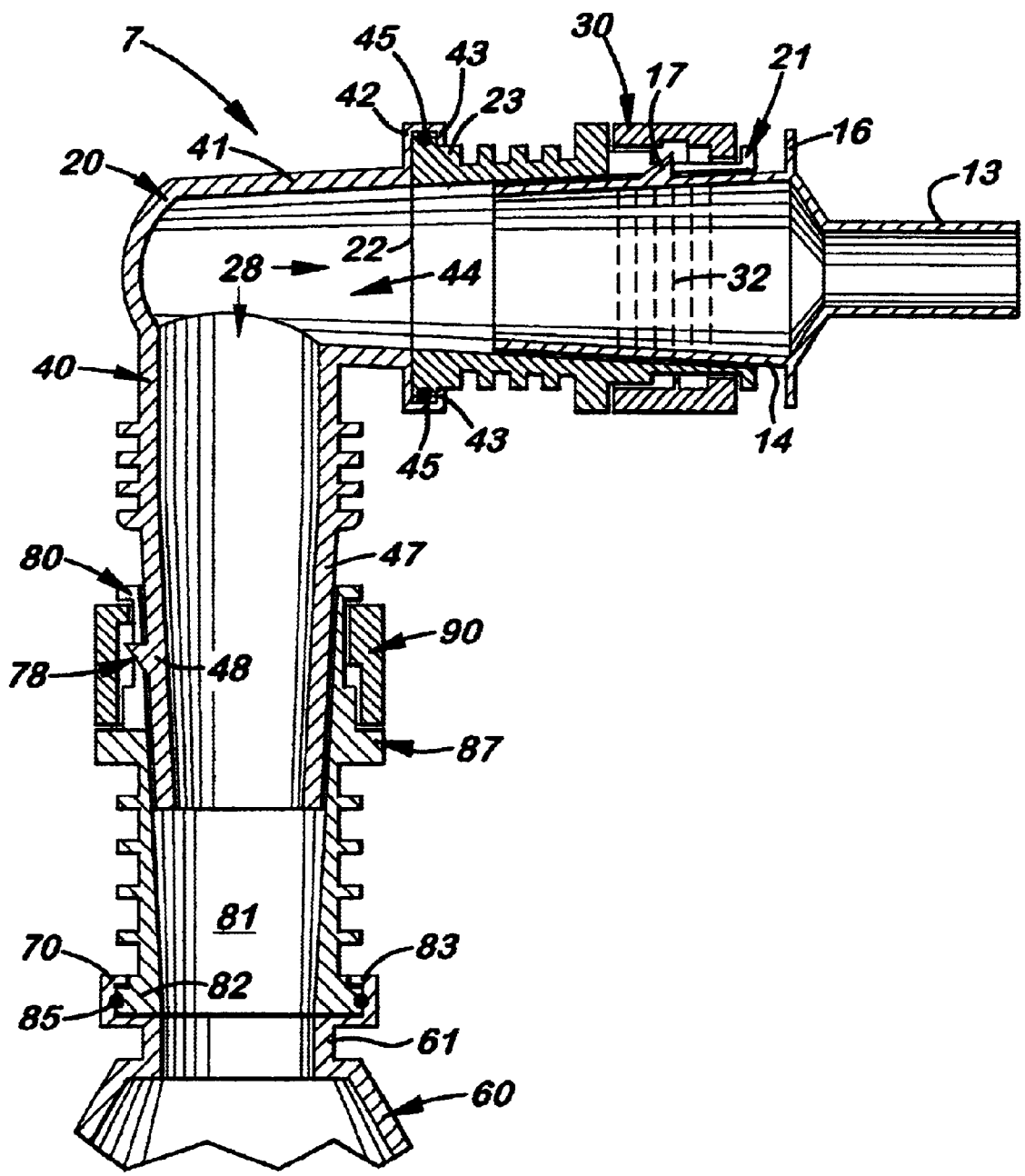
FIG. 3 is a sectional, side elevational view of the assembled system.
Figure 4:
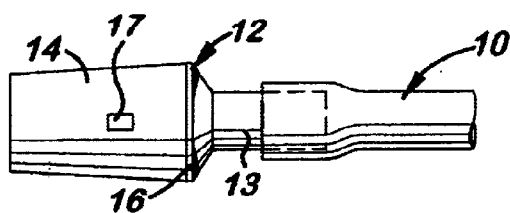
FIG. 4 is a top plan view of the end adapter attached to the main endotracheal tube section.
Figure 5:
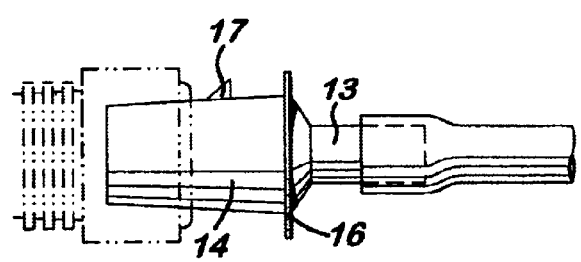
FIG. 5 is side elevational view of the end adapter attached to the modified ventilation tube shown in FIG. 4.
Figure 6:
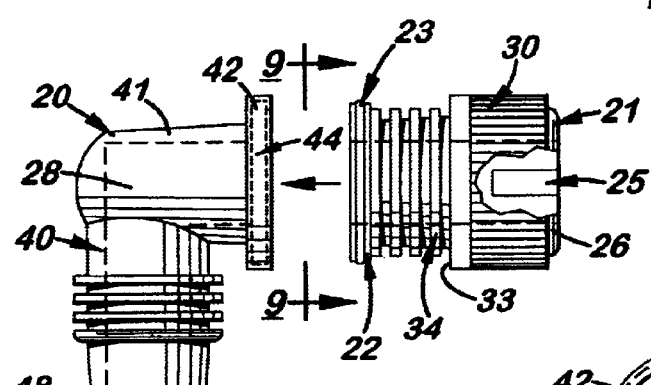
FIG. 6 is an end elevational view of the end adapter shown in FIGS. 4 and 5.
Figure 6:
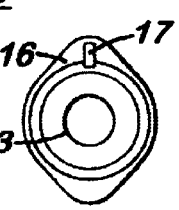
Figure 8:
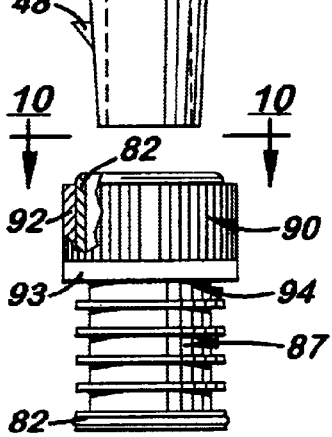
FIG. 8 is a rear elevational view of the long leg member used on the elbow connector's L-shaped leg member.
Figure 8:
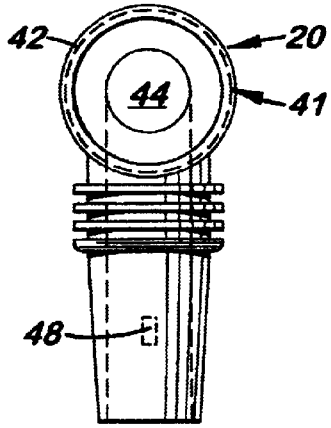

An improved ventilation tube connection system, generally designated as 7, is disclosed that includes a modified endotracheal tube 10, an elbow connector 20, and a modified ventilation tube 60. The modified endotracheal tube 10 is similar to a standard endotracheal tube with a standard main tube section 11 having an integrally formed or adhesively attached end adapter 12 located on its distal end. The end adapter 12, shown more clearly in FIGS. 3–5, is a hollow, cylindrical-shaped structure with a narrow main tube connecting section 13 and a wide section 14. Formed on the outer surface of the wide section 14 is a laterally extending key 17. The wide section 14 is slightly conical in shape and narrows towards its distal end. Integrally formed on the wide section 14, adjacent to the main tube connecting section 13, are laterally extending gripping ears 16 that, during use, may be held by medical personnel to connect the elbow connector 20 to the modified endotracheal tube 10. During assembly, the main tube connecting section 13 connects to the central passageway 24 formed in the modified endotracheal tube 10.

The elbow connector 20, shown more clearly in FIGS. 3, 7–10, includes a rotating leg member 21 and an L-shaped fixed leg member 40. The fixed leg member 40 includes a short leg section 41 and a perpendicularly aligned long leg section 47. Both the rotating leg member 21 and the fixed leg member 40 are hollow thereby providing a continuous passageway through the elbow connector 20 when connected together.

The rotating leg member 21 is conical-shaped, compatible, and slightly larger than the wide section 14 on the end adapter 12 so that the end adapter 12 may be forced tightly to the rotating leg member's central passageway 28. Formed on the distal end 22 of the rotating leg member 21 is a larger diameter circular receiver 23 that snap-fits into a larger diameter circular receiver 42 formed around the main opening 44 on the short leg member 41. The circular receiver 42 is slightly larger in diameter than the circular receiver 23 and includes an inward-directed lip 43 that prevents longitudinal movement and disengagement of the circular receiver 23 when pressed tightly therein. When initially connected together, the circular receiver 23 is able to rotate freely 360 degrees inside the circular receiver 42. An optional O-ring 45 is disposed between the inside surface of the circular receiver 42 and the outside surface of the circular receiver 23 to provide an airtight seal therebetween.

Figure 7:
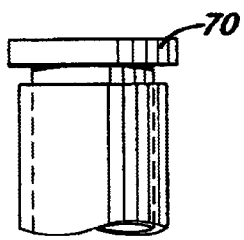
FIG. 7 is an exploded side elevational view of the ventilation tube connection system.
Figure 9:
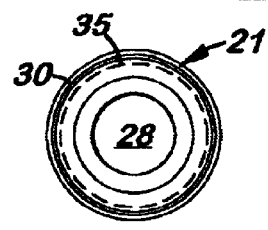
FIG. 9 is a front elevational view of the rotating leg member taken along line 9—9 in FIG. 7.

As shown in FIG. 7, a longitudinally aligned slot 25 is formed near the distal end 22 of the rotating leg member 21 which is designed to receive the key 17 formed on the outer surface on the end adapter 12 as shown in FIG. 4. When the end adapter 12 and rotating leg member 21 are longitudinally and axially aligned, and pressed together, the key 17 slides into the slot 25. The key 17 is sufficient in height to extend above the outer surface of the rotating leg member 21 when the key 17 is inserted into the slot 25, as shown in FIG. 3.

Disposed around the rotating leg member 21 is a first rotating collar 30 with a spiral groove 32 formed on its inside surface. The first rotating collar 30 has a transversely aligned end surface 33 with a central bore 34 formed therein slightly larger in diameter than the rotating leg member 21 so that the first rotating collar 30 may freely rotate and move longitudinally thereover. Advancement of the first rotating collar 30 towards the proximal end 26 of the rotating leg member 21 is prevented by the rotating leg member 21 conical shape. Also, formed on the collar 30 end surface 33 is a transversaly aligned slot 35 (see FIG. 9) that enables the key 17, formed on the end adapter 12, to be inserted through the central bore 34 on the first rotating collar 30 when the end adapter 12 is forced into the rotating leg member 21 passageway 28. When the end adapter 12 is inserted into the passageway 28, the key 17 is disposed inside the spiral groove 32 formed on the first rotating collar 30 (see FIG. 3). When the first rotating collar 30 is rotated, the key 17 follows the spiral groove 32 thereby pulling the end adapter 12 into the rotating leg member 21. Before tightening the first rotating collar 30, the user adjusts the relative position of the rotating leg member 21 on the elbow connector 20 and adjusts the relative position of the end adapter 12 on the rotating leg member 21. These two adjustment features allow the user to adjust the relative positions of the modified endotracheal tube 10 on the elbow connector 20. The fixed leg member 40 on the elbow connector 20 includes a cylindrical, conical, long leg section 47 which is similar in diameter to the wide section 14 on the end adapter 12. Formed on the outer surface of the long leg section 47 is a laterally extending key 48. During assembly, the long leg section 47 is forced into the central passageway 81 formed on the rotating coupler 80, discussed further below.

The modified ventilation tube 60 includes a main stem member 61 and a rotating coupler 80. In the preferred embodiment, the main stem member 61 is Y-shaped and connects to two ventilation branching tubes 63 and 64. Formed inside the main stem member 61 is a Y-shaped air passageway 62.

The rotating coupler 80 includes a straight, hollow member 87 and a second rotating collar 90. The hollow member 87 is conical-shaped and narrows towards its distal end, and complementary in shape to receive the long leg section 47 on the fixed leg member 40 described above. Formed on the distal end of the hollow member 87 is a wide circular receiver 82 similar to the circular receiver 42 formed on the short leg section 41. During assembly, the circular receiver 82 snap-fits into a wide circular base 70 formed on the main stem member 61. A lip 83 formed on the inside surface of the circular base 70 prevents longitudinal movement and disengagement of the circular receiver 82 from the circular base 70. An optional O-ring 85 is disposed between the circular base 70 and the inside surface of the circular receiver 82 to provide an airtight seal therebetween.

Formed near the distal end of the hollow member 87 is a longitudinally aligned slot 78 designed to receive the key 48 formed on the long leg section 47 on the fixed leg member 40. When the long leg section 47 is forced into the hollow member 87, the key 48 extends into the slot 78. Disposed around the hollow member 87 is a second rotating collar 90 with a spiral groove 92 formed on its inside surface designed to receive the key 48. The second rotating collar 90, which is similar to the first rotating collar 30 described above, has a transversely aligned end surface 93 with a central bore 94 formed therein so that the second rotating collar 90 may freely rotate around the hollow member 87. The central bore 94 is slightly larger in diameter than the hollow member 87 so that its longitudinal advancement over the hollow member 87 is permitted.

Figure 10:
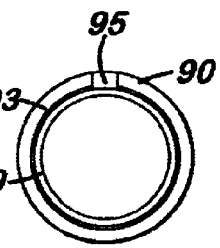
FIG. 10 is a top plan view of the rotating coupler taken along line 10—10 in FIG. 7.

As shown in FIG. 10, formed on the end surface 93 of the second rotating collar 90 is a transversely aligned slot 95 that enables the key 48 formed on the fixed leg member 40 to be inserted through the bore 94 of the second rotating collar 90 when the elongated wide section 47 is forced into the hollow member 87. When the second rotating collar 90 is rotated on the hollow member 87, the key 48 follows the spiral groove 92 and forces the fixed leg member 40 into the hollow member 87. Before tightening the second rotating collar 90, the user may adjust the relative position of the hollow member 87 on the main stem member 61 to adjust the relative position of the second rotating collar 90 to the hollow member 87.

In summary, both the rotating leg member 21, the rotating coupler 80, and the two collars 30, 90 enable the ends of the modified endotracheal and modified ventilation tubes 10, 60 to rotate around the adjoining rotating and fixed leg members 21, 40, respectively, to reduce torque exerted on the tubes 10, 60 and to provide greater comfort to the patient during use. If desired, the end adapter 12 on the modified endotracheal tube 10 may be connected directly to a manual ventilation bag (not shown). In addition, the elbow connector 20 may be removed so that the rotating coupler 80 may be directly connected to the end adapter 12.

In the preferred embodiment, the end adapter 12, the elbow connector 20, and the main stem member 61 are made of plastic. The end adapter 12 is approximately ½ inch in diameter and 2 inches in length. The rotating leg member 21 is approximately ¾ inch in diameter and 2 inches in length. The fixed leg member 40 is approximately ¾ inch in diameter and 2 inches in length. The hollow member 87 is approximately ¾ inch in diameter and 2 inches in length. The main stem member 61 is approximately ¾ inch in diameter and 3 inches in length.

Operation

The manner of use of this invention is quite easy when used by a qualified medical practitioner. The main tube section 11 on the modified endotracheal tube 10, is first inserted into the patient. The end adapter 12 on the modified endotracheal tube 10, that is protruding from the patient, is inserted into the distal end 22 of the rotating leg member 21. The end adapter 12 is aligned so that its key 17 may be inserted through the slot 35 formed on the first rotating collar 30. As the first rotating collar 30 is rated in a clockwise direction, the spiral groove 32 on the inside surface begins to narrow as it is rotated, thus exerting tension on the key 17. Although the connection is mechanical, the first rotating collar 30 may be easily rotated counterclockwise to release the key 17 from the first rotating collar 30. The position of the elbow connector 20 may be adjusted to reduce torque exerted thereon by the modified ventilation tube 60.

The fixed leg member 40 is now inserted into the rotating coupler 80 on the modified ventilation tube 60. The key 48 located on the fixed leg member 40 is inserted into the slot 95 formed on the hollow member 87. As described above, as the second rotating collar 90 is rotated in a clockwise direction, the spiral groove 92 on the inside diameter of the second rotating collar 90 begins to narrow as the second collar 90 is rotated, increasing the tension placed upon the key 48. This connection provides a mechanical connection, yet the second rotating collar 90 is easily rotated counterclockwise to release the key 48 from the second rotating collar 90 from the slot 95. The position of the main stem member 61 of the modified ventilation tube 60 may be adjusted to relieve torque exerted on the elbow connector 20.

Conclusions, Ramifications, and Scope

Accordingly, the reader will see that this invention provides safe, mechanical connections for those persons requiring mechanical ventilation assistance. Persons relying upon mechanical ventilation assistance are relying upon the tubing connections for breathing assistance and survival. Any disconnection of any of the tubing leading from the patient to a ventilator can be hazardous. These mechanical connections prevent the potentially fatal condition known as a "pop-off" and allow the tubing to be quickly disconnected if a person should require suctioning or manual ventilation assistance.

Although the descriptions above contain many specifications, these should not be construed as limiting the scope of the invention but as merely providing illustrations of some of the presently preferred embodiments of this invention. Thus the scope of the invention should be determined by the appended claims and their legal equivalents, rather than by the examples given.

I claim:

1. An improved ventilation tube connection system, comprising:

a. a modified endotracheal tube with an endotracheal main tube and an end adapter attached to said endotracheal main tube;

b. a hollow elbow connector including a rotating leg member and an L-shaped fixed leg member, said fixed leg member including a short leg section and a perpendicularly aligned long leg section, said rotating leg member being coupled to and allowed to freely rotate around said short leg section, said rotating leg member slidingly received into said end adapter on said modified endotracheal tube;

c. means to selectively secure said end adapter and said rotating leg member together;

d. a hollow modified ventilation tube including a rotating coupler adjustably connected to a main body, said main body being selectively connected to a ventilator, said rotating coupler able to slidingly receive said fixed leg member; and, e. means to selectively secure said rotating coupler to said long leg section on said fixed leg member together.

2. The ventilation tube connection system, as recited in claim 1, wherein said means to selectively secure said end adapter to said rotating leg member is a first rotating collar disposed around said rotating leg member, a key formed on said end adapter, and a slot formed on said rotating leg member; said first rotating collar including a spiral groove formed on its inside surface which engages said key so that when said end adapter is connected to said rotating leg member, said first rotating collar may be rotated to apply force against said key to hold said end adapter on said rotating leg member.

3. The ventilation tube connection system, as recited in claim 2, wherein said means to selectively secure said rotating coupler to said long leg section is a second rotating collar disposed around said rotating coupler, a slot formed on said rotating coupler, and key formed on said long leg section, whereby when said fixed leg member is connected to said rotating coupler, said key is disposed in said slot and said second rotating collar may be rotated to selectively apply force against said key and hold said long leg section on said rotating coupler.

4. The ventilation tube connection system, as recited in claim 3, wherein said end adapter and said rotating leg member are complementary in shape so that they may be slidingly forced together.

5. The ventilation tube connection system, as recited in claim 3, wherein said fixed leg member and said rotating coupler are complementary in shape so that they may be slidingly forced together.

6. The ventilation tube connection system, as recited in claim 5, further including an O-ring disposed between said rotating leg member and said short leg section.

7. The ventilation tube connection system, as recited in claim 6, further including an O-ring disposed between said rotating coupler and said modified ventilation tube.

8. The ventilation connection tube system, as recited in claim 3, wherein said rotating coupler and said main body of said modified ventilation tube are snap-fitted together.

9. The ventilation tube connection system, as recited in claim 2, wherein said rotating leg member and said short leg member are snap-fitted together.

10. An improved ventilation tube connection system, comprising:
 a. a modified endotracheal tube with an endotracheal main tube and an end adapter attached to said endotracheal main tube;
 b. a hollow elbow connector including a rotating leg member and an L-shaped fixed leg member, said fixed leg member including a perpendicularly aligned short leg section and a perpendicularly aligned long leg section, said rotating leg member being coupled to and allowed to freely rotate around said short leg section;
 c. means to selectively secure said end adapter and said rotating leg member together;
 d. a hollow modified ventilation tube including a rotating coupler adjustably connected to a main body, said main body capable of being selectively connected to a ventilator, said rotating coupler able to selectively receive said fixed leg member; and,
 e. means to selectively secure said rotating coupler and said fixed leg member together.

11. The ventilation tube connection system, as recited in claim 10, wherein said means to selectively secure said end adapter to said rotating leg member is a first rotating collar disposed around said rotating leg member, a key formed on said end adapter, and a slot formed on said rotating leg member; said first rotating collar including a spiral groove formed on its inside surface which engages said key so that when said end adapter is connected to said rotating leg member, said first rotating collar may be rotated to apply force against said key to hold said end adapter on said rotating leg member.

12. The ventilation tube connection system, as recited in claim 11, wherein said means to selectively-connect said rotating coupler to said fixed leg member is a second rotating collar disposed around said rotating coupler and a slot formed on said rotating coupler and a key formed on said fixed leg member, whereby when said fixed leg member is connected to said rotating coupler, said key is disposed in said slot and said second collar may be rotated to selectively apply force against said key and hold said fixed leg member on said rotating coupler.

13. The ventilation tube connection system, as recited in claim 10, wherein said end adapter and said rotating leg member are complementary in shape so that they may be slidingly forced together.

14. The ventilation tube connection system, as recited in claim 10, wherein said fixed leg member and said rotating coupler are complementary in shape so that they may be slidingly forced together.

15. The ventilation tube connection system, as recited in claim 10, wherein said rotating leg member and said short leg section are able to snap-fit together.

16. The ventilation tube connection system, as recited in claim 10, wherein said rotating coupler and said main body of said modified ventilation tube are able to snap-fit together.

17. The ventilation tube connection system, as recited in claim 10, further including an O-ring disposed between said rotating leg member and said short leg section.

18. The ventilation tube connection system, as recited in claim 10, further including an O-ring disposed between said rotating coupler and said modified ventilation tube.

19. An improved ventilation tube connection system, comprising:
 a modified endoiracheal tube with an endotrachcal main tube and an end adapter attached to said endotracheal main tube;
 b. a hollow elbow connector including a rotating leg member and an L-shaped fixed leg member, said fixed leg member including a perpendicularly aligned short leg section and a perpendicularly aligned long leg section, said rotating leg member being coupled to and allowed to freely rotate around said short leg section;
 c. a first rotating collar disposed around said rotating leg member and a key formed on said end adapter and a slot formed on said rotating leg member; said first rotating collar including a spiral groove formed on its inside surface which engages said key so that when said end adapter is connected to said rotating leg member, said first rotating collar may be rotated to apply force against said key to hold said end adapter on said rotating leg member;
 d. a hollow modified ventilation tube including a rotating coupler adjustably connected to a main body, said main body capable of being selectively connected to a ventilator, said rotating coupler able to selectively receive said fixed leg member; and,
 e. a second rotating collar disposed around said rotating coupler and a slot formed on said rotating coupler and key formed on said fixed leg member, whereby when said fixed leg member is connected to said rotating coupler, said key is disposed in said slot and said second collar may be rotated to selectively apply force against said key and hold said fixed leg member on said rotating coupler.

\* \* \* \* \*